US011649437B2

(12) United States Patent
Bollard et al.

(10) Patent No.: US 11,649,437 B2
(45) Date of Patent: *May 16, 2023

(54) GENERATING HPV ANTIGEN-SPECIFIC CELLS FROM A NAIVE T CELL POPULATION

(71) Applicant: CHILDREN'S NATIONAL MEDICAL CENTER, Washington, DC (US)

(72) Inventors: Catherine M. Bollard, Washington, DC (US); Conrad Russell Cruz, Washington, DC (US); Patrick J. Hanley, Washington, DC (US); Michael Keller, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 223 days.

This patent is subject to a terminal disclaimer.

(21) Appl. No.: 17/152,149

(22) Filed: Jan. 19, 2021

(65) Prior Publication Data
US 2021/0163892 A1 Jun. 3, 2021

Related U.S. Application Data

(62) Division of application No. 15/771,648, filed as application No. PCT/US2016/059683 on Oct. 31, 2016, now Pat. No. 10,934,525.

(60) Provisional application No. 62/248,818, filed on Oct. 30, 2015.

(51) Int. Cl.
A61K 35/17 (2015.01)
C12N 5/0783 (2010.01)
A61P 31/00 (2006.01)
A61P 37/04 (2006.01)
A61P 15/00 (2006.01)
C07K 14/54 (2006.01)
C07K 14/55 (2006.01)
C07K 14/73 (2006.01)
C07K 14/705 (2006.01)

(52) U.S. Cl.
CPC ............ C12N 5/0636 (2013.01); A61K 35/17 (2013.01); A61P 15/00 (2018.01); A61P 31/00 (2018.01); A61P 37/04 (2018.01); C07K 14/5412 (2013.01); C07K 14/5418 (2013.01); C07K 14/5434 (2013.01); C07K 14/5443 (2013.01); C07K 14/55 (2013.01); C07K 14/70514 (2013.01); C07K 14/70517 (2013.01); C07K 14/70521 (2013.01); C12N 2501/2302 (2013.01); C12N 2501/2307 (2013.01); C12N 2501/2315 (2013.01); C12N 2501/59 (2013.01); C12N 2502/1121 (2013.01); C12N 2502/1157 (2013.01)

(58) Field of Classification Search
None
See application file for complete search history.

(56) References Cited

U.S. PATENT DOCUMENTS

| 10,934,525 | B2 | 3/2021 | Bollard et al. |
|---|---|---|---|
| 2007/0014810 | A1 | 1/2007 | Baker et al. |
| 2007/0212767 | A1 | 9/2007 | Bonyhadi et al. |
| 2011/0182870 | A1 | 7/2011 | Leen et al. |
| 2013/0058909 | A1 | 3/2013 | Szabolcs |
| 2014/0134142 | A1 | 5/2014 | Smith et al. |
| 2015/0273053 | A1 | 10/2015 | Goronzy et al. |
| 2015/0359876 | A1 | 12/2015 | Bollard et al. |
| 2017/0028052 | A1 | 2/2017 | Ramos et al. |
| 2018/0072990 | A1 | 3/2018 | Bollard et al. |
| 2021/0155900 | A1 | 5/2021 | Bollard et al. |
| 2021/0163892 | A1 | 6/2021 | Bollard et al. |
| 2021/0380943 | A1 | 12/2021 | Bollard et al. |

FOREIGN PATENT DOCUMENTS

| CA | 2 980 039 A1 | 9/2016 |
|---|---|---|
| EP | 3 368 051 A4 | 6/2019 |
| JP | 2006524991 | 11/2006 |
| JP | 2015501651 | 1/2015 |
| WO | WO 2002/08435 | 1/2002 |
| WO | WO 02/22648 A2 | 3/2002 |
| WO | WO 2009/002159 A2 | 12/2008 |
| WO | WO 2011/028351 A1 | 3/2011 |
| WO | WO 2012/099973 | 7/2012 |
| WO | WO 2013/088148 | 6/2013 |
| WO | WO 2014/031687 | 2/2014 |
| WO | WO 2015/009604 A1 | 1/2015 |
| WO | WO 2015/095895 | 6/2015 |
| WO | WO 2015/112626 A9 | 7/2015 |
| WO | WO 2016/154112 | 9/2016 |
| WO | WO 2017/075571 A1 | 5/2017 |

OTHER PUBLICATIONS

Combined Chinese Office Action and Search Report dated May 31, 2021 in Chinese Patent Application No. 201680070159.8 (with English Translation), 19 pages.

Carlos A. Ramos, et al., "Human Papillomavirus Type 16 E6/E7-specific Cytotoxic T Lymphocytes for Adoptive Immunotherapy of HPV-associated Malignancies", J Immunother, vol. 36 No. 1, Jan. 31, 2013, pp. 66-76.

Marcus O. Butler, et al., "A Panel of human cell-based artificial APC enables the expansion of long-lived antigen-specific CD4+ T cells restricted by prevalent HLA-DR alleles", International Immunology, vol. 22 No. 11, Nov. 8, 2010, pp. 863-873.

Japanese Office Action dated Jul. 20, 2021 in Japanese Patent Application No. 2018-522517 (with English language translation), 7 pages.

European Office Action dated Sep. 14, 2022 in European Patent Application No. 16861028.5, 4 pages.

Office Action dated Feb. 22, 2022 in corresponding European Patent Application No. 16 861 028.5, 6 pages.

(Continued)

Primary Examiner — Nianxiang Zou
(74) Attorney, Agent, or Firm — Oblon, McClelland, Maier & Neustadt, L.L.P.

(57) ABSTRACT

Safe, rapid and efficient methods for producing antigen-specific T cells recognizing human papilloma virus or HPV antigens.

26 Claims, 3 Drawing Sheets

(56) References Cited

OTHER PUBLICATIONS

International Search Report and Written Opinion dated Mar. 2, 2017 in PCT/US2016/059683 filed Oct. 31, 2016.
Office Action dated Aug. 25, 2020, in Japanese patent application No. 2 0 1 8- 5 2 2 5 1 7, w/translation ( 31 pages).
Extended European Search Report dated May 28, 2019 in European Patent Application No. 16861028.5, 8 pages.
Hanley, P.J., et al., "CMV-specific T cells generated from naïve T cells recognize atypical epitopes and may be productive in vivo", Immunotherapy, vol. 7 No.285, Retrieved from the internet: URL: https://www.ncbi.nlm.nih.gov/pubmed/25925682, Apr. 29, 2015, XP055588609, pp. 1-12 with cover page.
Hanley, P.J., et al., "Functionally active virus-specific T cells that target CMV, Adenovirus, and EBV can be expanded from naïve T-cell populations in cord blood and will target a range of viral epitopes", Blood, vol. 114 No. 9, XP055200362, Aug. 27, 2009, pp. 1958-1967 with cover page.
Mccormack, S.E., et al., "Human papilloma virus-specific T cells can be generated from naïve T cells for use as an immunotherapeutic strategy for immunocompromised patients", Cytotherapy, vol. 20 No. 3, Mar. 1, 2018, XP055588588, pp. 385-393.
Almajhdi FN, Senger T, Amer HM, Gissmann L, O "HLSCHLA" Ger P (2014) Design of a Highly Effective Therapeutic HPV16 E6/E7-Specific DNA Vaccine: Optimization by Different Ways of Sequence Rearrangements (Shuffling). PLOS ONE 9(11): E113461. DOI:10.1371/ Journal. Pone. 0113461.
Bao L, et al.: Expansion of Cytomegalovirus PP65 and IE-1 Specific Cytotoxic T Lymphocytes for Cytomegalovirus-Specific Immunotherapy Following Allogeneic Stem Cell Transplantation. Biol Blood Marrow Transplant 14: 1156-1162 (2008).
Bao L, et al.: In Vitro Generation of Cytotoxic T Lymphocytes Against MAGE A1 and MAGE A3 Derived From Healthy Donors. Blood., 114:4079 (2009).
Bao L., et al.: Upregulation of MAGE-A1, MAGE-A3, NY-ESO-1 and MHC Molecules on Neuroblastoma Cells Following Exposure to Decitabine and Interferon-Γ. Blood, 116:5179 (2010).
Bollard C., et al.: Complete Tumor Responses in Lymphoma Patients who Receive Autologous Cytotoxic T Lymphocytes Targeting EBV Latent Membrane Proteins. Blood, 112:230 (2008).
Bollard C., et al.: Cytotoxic T Lymphocytes (CTL) Specific for Multiple Viruses can be Generated From Umbilical Cord Blood for Adoptive Immunotherapy. Biology of Blood and Marrow Transplantation, vol. 14, Issue 2, p. 16 Published in Issue: Feb. 2008.
Brenner M., et al.: Rapid Generation of Antigen-Specific T Cells for Pre-Clinical and Clinical Applications Using a Novel Mini Cell Bioreactor. Biology of Blood and Marrow Transplantation, vol. 15, Issue 2, p. 137 (Feb. 2009).
Cid-Arregui, Angel Therapeutic Vaccines Against Human Papillomavirus an Cervical Cancer. The Open Virology Journal, 2009, 3, 67-83.
Cruz C.R., et al.: Immune-Based Therapies Targeting MAGE-A4 for Relapsed/Refractory Hodgkin's Lymphoma After Stem Cell Transplant. Blood, 114:4089 (2009).
Cruz C.R., et al.: Production of MAGE-A4-Specific CTL From Healthy Donors, Patients, and Cord Blood for Lymphoma Therapy After Transplant. Biology of Blood and Marrow Transplantation, vol. 15, Issue 2, p. 65 (Feb. 2009).
Deveraj et al. Development of HPV Vaccines for HPV-Associated Head and Neck Squamous Cell Carcinoma. Crit Rev Oral Biol Med, 14(5):345-362 (2003).
Dienz and Rincon the Effects of IL-6 on CD4 T Cell Responses. Clin Immunol. Jan. 2009 ; 130(1): 27/33.
Dolfi et al. Dendritic Cells and CD28 Costimulation are Required to Sustain Virus-Specific CD8+ T Cell Responses During the Effector Phase In Vivo. J Immunol Apr. 15, 2011, 186 (8) 4599-4608.
Eskander et al. Immunotherapy: An Evolving Paradigm in the Treatment of Advanced Cervical Cancer. Clinical Therapeutics/vol. 37, No. 1, Jan. 2015.

Foster A E, Dotti G, Lu A, et al. Antitumor Activity of EBV-Specific T Lymphocytes Transduced With a Dominant Negative TGF-Beta Receptor. Journal of Immunotherapy. 2008; 31:500-505.
Fujita Y., et al.: Exploiting Cytokine Secretion to Rapidly Produce Multivirus-Specific T Cells for Adoptive Immunotherapy Blood, 112:4594 (2008).
Gagnon et al. IL-6, in Synergy With IL-7 or IL-15, Stimulates TCR-Independent Proliferation and Functional Differentiation of CD8+ T Lymphocytes. J Immunol 2008; 180:7958-7968.
Gerdemann, et al.: Broad Spectrum Tumor Antigen-Specific Cytotoxic T Lymphocytes (CTL) for Therapy of Hematological Malignancy. Blood., 114:4083 (2009).
Gerdemann, et al.: Multi-Tumor-Antigen-Specific Cytotoxic T Lymphocytes for Therapy of Hematologic Malignancies. Biology of Blood and Marrow Transplantation, vol. 16, Issue 2, S179 Published in Issue: Feb. 2010.
Gerdemann U., et al.: Multivirus-Specific T Cell Immunotherapy to Prevent or Treat Infections of Stem Cell Transplant Recipients. Blood, 112:2207 (2008).
Gerdemann et al. Cytotoxic T Lymphocytes Simultaneously Targeting Multiple Tumor-Associated Antigens to Treat EBV Negative Lymphoma. Mol Ther. Dec. 2011; 19(12): 2258- 2268.
Gervois et al. High Avidity Melanoma-Reactive Cytotoxic T Lymphocytes are Efficiently Induced From Peripheral Blood Lymphocytes on Stimulation by Peptide-Pulsed Melanoma Cells. Clinical Cancer Research vol. 6, 1459-1467, Apr. 2000.
Grabowska et al. Identification of Promiscuous HPV16-Derived T Helper Cell Epitopes for Therapeutic HPV Vaccine Design. Int. J. Cancer: 136, 212-224 (2015).
Hanley et al.: Cytotoxic T Lymphocytes (CTL) Specific for Adenovirus and CMV Can be Generated From Umbilical Cord Blood for Adoptive Immunotherapy. Biology of Blood and Marrow Transplantation, vol. 15, Issue 2, p. 17-18 Published in Issue: Feb. 2009.
Hanley P J, Melenhorst J J, Nikiforow S, et al. CMV-Specific T Cells Generated From Naive T Cells Recognize Atypical Epitopes and May be Protective In Vivo. Science Translational Medicine. 2015; 7:285RA263.
Hanley P J, Lam S, Shpall E J, Bollard C M. Expanding Cytotoxic T Lymphocytes From Umbilical Cord Blood That Target Cytomegalovirus, Epstein-Barr Virus, and Adenovirus. Journal of Visualized Experiments: Jove. 2012: E3627.
Heslop H E, Slobod K S, Pule M A, et al. Long-Term Outcome of EBV-Specific T-Cell Infusions to Prevent or Treat EBV-Related Lymphoproliferative Disease in Transplant Recipients. Blood. 2010; 115:925-935.
Hoots B E, Palefsky J M, Pimenta J M, Smith J S. Human Papillomavirus Type Distribution in Anal Cancer and Anal Intraepithelial Lesions. International Journal of Cancer. 2009; 124:2375-2383.
De Jong et al. Human Papillomavirus Type 16-Positive Cervical Cancer is Associated With Impaired CD4+ T-Cell Immunity Against Early Antigens E2 and E6. Cancer Research. 2004; 64:5449-5455.
Leen et al. Improving T Cell Therapy for Cancer. Annu. Rev. Immunol. 2007. 25: 243-65.
Leen A M, Bollard C M, Mendizabal A M, et al. Multicenter Study of Banked Third-Party Virus-Specific T Cells to Treat Severe Viral Infections After Hematopoietic Stern Cell Transplantation. Blood. 2013; 121:5113-5123.
Leen A., et al.: Overcoming Antigenic Competition to Produce Multispecific Cytotoxic T Lymphocyte Lines for Adoptive Transfer. Biology of Blood and Marrow Transplantation, vol. 15, Issue 2, p. 134 (Feb. 2009).
Liu G. et al. Cytotoxic T-Lymphocyte Responses to Human Papillomavirus Type 16 E5 and E7 Proteins and HLA-A*0201-Restricted T-Cell Peptides in Cervical Cancer Patients. Journal of Virology, Mar. 2007, p. 2869-2879.
Lucas K., et al.: Rapid Generation of Cytomegalovirus Specific T Lymphocytes Using Commercially Available CMV PP65 Peptides. Blood, 108:5144 (2006).
Mahdavi et al. Vaccines Against Human Papillomavirus and Cervical Cancer: Promises and Challenges. The Oncologist 2005; 10: 528-538.
Melenhorst J J, Castillo P, Hanley P J, et al. Graft Versus Leukemia Response Without Graft-Versus-Host Disease Elicited by Adop-

(56) References Cited

OTHER PUBLICATIONS tively Transferred Multivirus-Specific T-Cells. Molecular Therapy: The Journal of the American Society of Gene Therapy. 2015; 23:179-183.

Morandi F., et al.: Tumor MRNA-Transfected Dendritic Cells Stimulate the Generation of CTL That Recognize Neuroblastoma-Associated Antigens and Kill Tumor Cells: Immunotherapeutic Implications. Neoplasia, vol. 8, No. 10, Oct. 2006, pp. 833-842.

Nakagawa et al. Persistence of Human Papillomavirus Type 16 Infection is Associated With Lack of Cytotoxic T Lymphocyte Response to the E6 Antigens. The Journal of Infectious Diseases 2000; 182: 595-8.

NCT02280811 T Cell Receptor Immunotherapy Targeting HPV-16 E6 for HPV-Associated Cancers: Sep. 6, 2017 Avaialble at https://clinicaltrials.gov/ct2/show/nct02280811.

NCT02379520 HPV-1618 E6E7-Specific T Lymphocytes, Relapsed HPV-Associated Cancers, Hestia (Hestia): Dec. 13, 2018 Available at: https://clinicaltrials.gov/ct2/show/nct02379520.

Ngo M C, Ando J, Leen A M, et al. Complementation of Antigen-Presenting Cells to Generate T Lymphocytes With Broad Target Specificity. J Immunother. 2014; 37:193-203.

Nimako et al. Human Papillomavirus-Specific Cytotoxic T Lymphocytes in Patients With Cervical Intraepithelial Neoplasia Grade III. Cancer Research 57. 4855-4861. Nov. 1, 1997.

Papadopoulou A, Gerdemann U, Katari U L, et al. Activity of Broad-Spectrum T Cells as Treatment for ADV, EBV, CMV, BKV, and HHV6 Infections After HSCT. Science Translational Medicine. 2014; 6:242RA283.

Quintarelli et al.: Cytotoxic T Lymphocytes Directed to the Preferentially Expressed Antigen of Melanoma (Prame) Target Chronic Myeloid Leukemia. Blood, Sep. 1, 2008;112(5): 1876-85. DOI: 10.1182/BLOOD-2008-04-150045. Epub Jun. 30, 2008.

Quintarelli et al.: Polyclonal Prame-Specific Cytotoxic T Lymphocytes Generated Using Protein-Spanning Pools of Overlapping Pentadecapeptides Target Chronic Myeloid Leukemia. Biology of Blood and Marrow Transplantation, Feb. 2009, vol. 15, Issue 2, 58-59.

Rooney C M, Leen A M, Vera J F, Heslop H E. T Lymphocytes Targeting Native Receptors. Immunological Reviews. 2014; 257:39-55.

Rosales et al. Immune Therapy for Human Papillomaviruses-Related Cancers. World J Clin Oncol Dec. 10, 2014; 5(5): 1002-1019.

Stamer et al. Generation of Cytomegalovirus PP65-Specific T Cells From Seronegative Donors. Blood., 110:4860 (2007).

Steele et al. T-Cell Responses to Human Papillomavirus Type 16 Among Women With Different Grades of Cervical Neoplasia. British Journal of Cancer (2005) 93, 248-259.

Stevanovic et al. Complete Regression of Metastatic Cervical Cancer After Treatment With Human Papillomavirus-Targeted Tumor-Infiltrating T Cells. J Clin Oncol 33:1543-1550 May 2015.

Torikai et al. Toward Eliminating HLA Class I Expression to Generate Universal Cells From Allogeneic Donors. Blood, Aug. 22, 2013 X vol. 122, No. 8.

Vera J., et al.: Rapid Generation of Antigen-Specific T Cells for Pre-Clinical and Clinical Applications Using a Novel Mini Cell Bioreactor Blood, 112:208 (2008).

Welten et al. CD27-CD70 Costimulation Controls T Cell Immunity During Acute and Persistent Cytomegalovirus Infection. J Virol. Jun. 2013; 87(12): 6851-6865.

Canadian Office Action dated Dec. 1, 2022 in Canadian Patent Application No. 3,003,678, 5 pages.

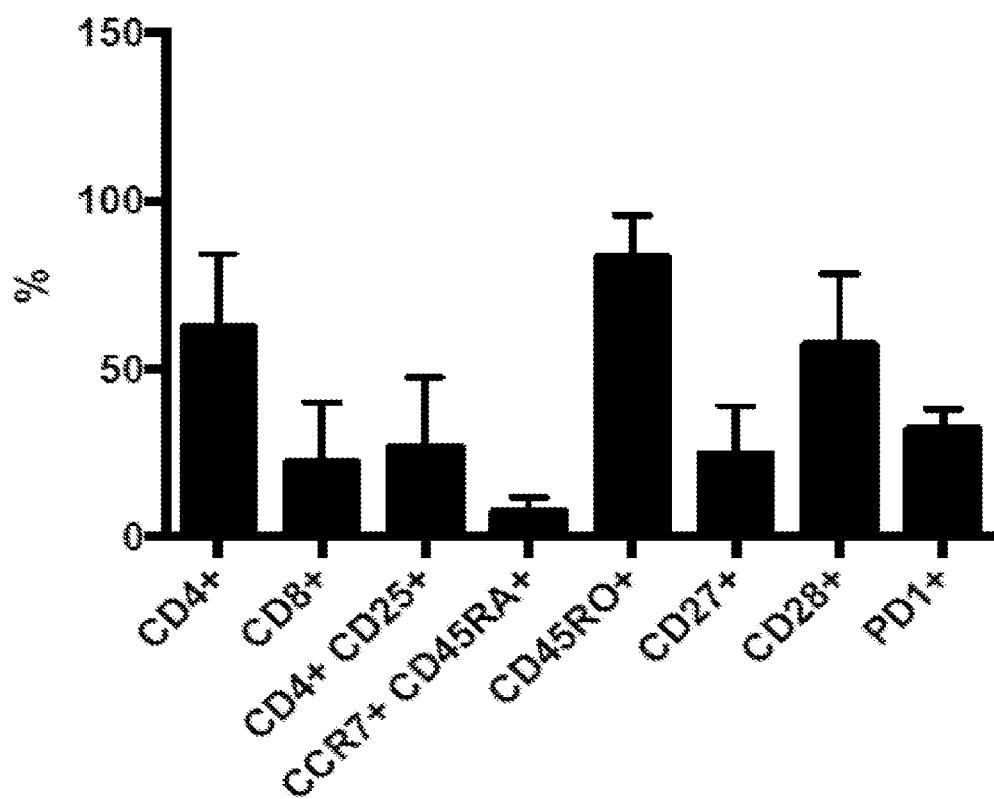

GENERATING HPV ANTIGEN-SPECIFIC CELLS FROM A NAIVE T CELL POPULATION

CROSS-REFERENCE(S) TO RELATED APPLICATIONS

This application is divisional of U.S. application Ser. No. 15/771,648, filed Apr. 27, 2018, which is the National Stage of International Application no. PCT/JP2016/059683, filed Oct. 31, 2016, which claims priority to U.S. Provisional Application No. 62/248,818, filed Oct. 30, 2015, which is incorporated by reference. This application is related to PCT/US2016/23413, filed Mar. 21, 2016 entitled "Generating virus or other antigen-specific cells for a naïve T cell population", which claims priority to U.S. Provisional Application Nos. 62/135,851 and 62/135,888, filed Mar. 20, 2015; and is related to PCT/US2014/62698, filed Oct. 28, 2014, entitled "Expansion of CMV-Specific T cells from CMV-Seronegative Donors", which claims priority to U.S. Provisional Application No. 61/896,296, filed Oct. 28, 2013. All of the above documents are incorporated by reference.

STATEMENT REGARDING FEDERALLY SPONSORED RESEARCH OR DEVELOPMENT

This research was sponsored in part by a grant from the National Cancer Institute of the National Institutes of Health, grant #: NCI PO1 CA148600-02 awarded to Catherine M. Bollard and Elizabeth J. Shpall.

BACKGROUND OF THE INVENTION

Field of the Invention

The invention involves human papilloma virus- or HPV-antigen-specific T cells and methods for producing them from the T cells of healthy or naïve donors as well as a cell-based therapy using these HPV-specific T cells for the treatment of diseases, disorders or conditions caused by or associated with human papilloma virus.

Description of the Related Art

Some current T-cell based immunotherapies use virus- and tumor-specific T cells expanded from samples containing T cells and precursor T cells. Virus-specific T cells have been shown to be effective against viral infections after stem cell transplantation. T cell based cell therapies using virus-specific T-cell populations can provide protection from virus-infected cells and are associated with fewer side effects than antiviral drugs.[1]. T cell based therapies using expanded virus-specific populations have activity against virus-expressing malignancies[2,3] and induced a graft-versus-leukemia effect that cleared circulating leukemic blasts.[4]

These immunotherapies have the advantage of providing lifelong protection due to the generation of memory cell populations.[3] Cells from samples having memory T cells are easily expanded ex vivo because the donors from which they are derived have previously encountered these pathogens, and hence, there are existing memory, virus-specific T cells that rapidly expand ex vivo.[5] More importantly, studies have shown that a single HLA match is enough to mediate therapeutic efficacy of these T cells, with minimal side effects. Therefore, banks of third party cells can be generated and maintained, for off the shelf use of such products.

Unfortunately for certain viral infections and virus-associated tumors not all potential sources of these cells have been previously exposed to the pathogen. One important example is HPV, which causes HPV infection in immune compromised hosts[6-8] and HPV-associated malignancies like cervical cancer.[9-14] In the United States, seroprevalence for any of the 9 HPV types is limited to approximately 40% for females and 20% for males.[15] Most donors are therefore naïve to HPV antigens. This imposes obstacles to expansion of HPV-recognizing T cells from these samples due to the absence of memory T cells.

It is difficult to expand antigen-specific T cells from these naïve cell populations, such as naïve T cells from unexposed/seronegative healthy donors or T cells from cord blood, because these T cells have never been primed by the antigen in vivo. Such populations lack antigen-specific memory T cells that can be readily expanded. In other settings, proposed methods for expanding such antigen-specific T cells from naïve donors currently use viruses, virus-infected cells, or virus-transformed cells.[16,17]

Methods that involve the use of viruses to produce antigen-specific T cells for therapeutic use are undesirable because they are associated with increased clinical risks and significant regulatory hurdles. It is for this reason that antigens in the form of peptides have been used to expand antigen-specific T cells.[18]

Application of these peptide-based methods towards generating HPV-specific T cells from naïve donors have met very limited success.[12]

Most successful attempts at generating T cells specific for HPV used autologous cells from a patient who had been previously exposed to HPV antigens. In one such study, although more than 1,200-fold expansion was seen, this was mostly limited to 8/156 cervical cancer patients and 33/52 oropharyngeal cancer patients and only 1/20 healthy donors where the responding donor was believed to behave been previously exposed to HPV antigens.[12]

For third party bank applications, it is crucial to generate HPV-specific T cells from healthy donors regardless of previous exposure to HPV antigens.

BRIEF SUMMARY OF THE INVENTION

The method according to the invention advantageously permits the rapid and robust expansion of HPV-recognizing or HPV-specific T cells, provides T cells which recognize therapeutically important antigens targeting opportunistic HPV infections and HPV-associated malignancies, and does not require the use of live viruses or virus-transformed cells. Here the inventors describe a new way of manufacturing these cells in a clinically-appliable way for use as a donor-derived and off-the-shelf product. The inventors leveraged their experience in generating T cell responses from naïve cell sources ex vivo to manufacture HPV-recognizing or HPV-specific T cells. Based on the immunological properties of HPV, the inventors modified the process of generating antigen-presenting dendritic cells, modified the concentration of cytokines used for expanding T cells, and used artificial APCs to help expand T cell numbers.

In one of its embodiments, the invention provides a robust method for generating HPV antigen-specific T cells (or HPV antigen-recognizing T cells). The generated HPV recognizing T cells may recognize a single epitope of an HPV antigen, multiple epitopes of a single HPV antigen or may recognize epitopes on different HPV antigens. The method employs overlapping peptide libraries of HPV antigen(s) pulsed onto different antigen presenting cells, such as dendritic cells, monocytes, K562 cells, artificial antigen presenting cells, PHA blasts, B-blasts, lymphoblastoid cells, and CD3-28 blasts, different priming and expansion cytokines—including but not limited to IL2, IL7, IL15)—and different selection methods (CD45RO depletion, etc)[16, 17] Other artificial or alternative antigen presenting cells may also be used. The antigen-specific T cells produced by the invention can be used to treat post-transplant viral infections and tumor relapse. These antigen-specific T cells and their precursors can be advantageously banked or stored for later administration to a subject in need of T-cell immunity against a particular pathogen or neoplastic condition.

The present invention comprises a process to specifically generate HPV antigen-specific T cells from the immune system of healthy donors, most of whom will be HPV seronegative and thus have virus-naïve T cell populations. The invention is a process and its use aimed at preventing viral infections after transplant and in other immunocompromised settings and circumstances where HPV can be problematic, like HPV-associated malignancies. The invention makes multi-HPV-antigen-specific T cells from naïve T cells in a clinically-relevant way that has never been done before from naïve T cells.

Because the invention itself is a process and use, it can be readily applied to generating antigen-specific responses from naïve populations against other opportunistic viruses, such as, but not limited to, HHV6 and BK virus. It can be expanded to include virus-specific antigens from diseases associated with malignancies such as but not limited to EBV and HIV. It can be combined with other cell products, lymphodepleting regimens, and epigenetic-modifying drugs. Other medical uses include promoting engraftment and providing a therapy to immunodeficient patients before a transplant.

The invention generates HPV-specific T cells using different overlapping peptide libraries pulsed onto potentially different antigen presenting cells (dendritic cells, monocytes, K562 cells, PHA blasts, B-blasts, lymphoblastoid cells, and CD3-28 blasts), different priming and expansion cytokines (including but not limited to IL2, IL7, IL15), and different selection methods (CD45RO depletion, etc). Other artificial or alternative antigen presenting cells may be used as well. The inventors also describe a third party bank of the said cells manufactured from naïve T cells, along with the process of selecting the best match for a donor.

The process of the present invention is safe, simple, rapid and reproducible and can be used to produce HPV-recognizing or HPV-specific T cells in accordance with good manufacturing practices (GMP) for a variety of different patients.

BRIEF DESCRIPTION OF THE DRAWINGS

FIG. 3. T cells that recognize HPV (n=5) have a mixed phenotype (CD4 and CD8), which has been shown to promote better responses from T cell infusions. Cells also express the costimulatory receptors CD27 and CD28.

DETAILED DESCRIPTION OF THE PREFERRED EMBODIMENTS

Figure 1:
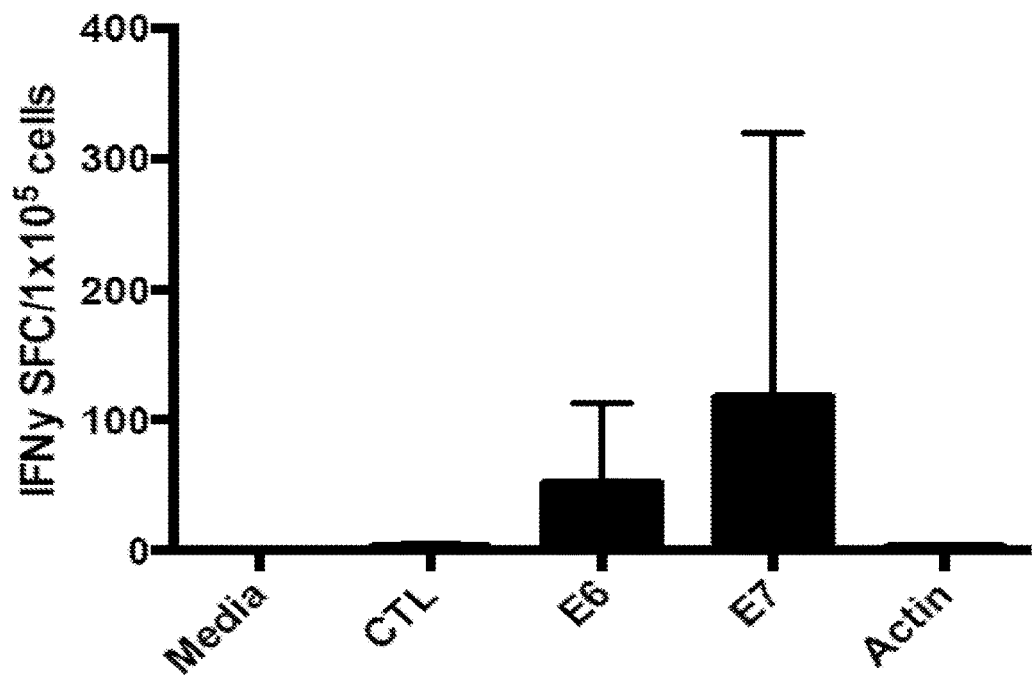
FIG. 1. T cells that recognize HPV were generated using the method disclosed herein from healthy donors (n=5). They specifically recognize HPV antigens E6 and E7 as compared to an irrelevant antigen (the self-protein actin). Background responses from cells alone (CTL) are shown. This shows that the process of the invention generates HPV specific T cells from healthy donors.

"Accessory cell" is a cell, such as a K562 cell, that provides costimulation for recognition of peptide antigens by T cells or that otherwise assists a T-cell recognize, become primed or expand in the presence of a peptide antigen. Accessory cells may also be other artificial or alternative antigen presenting cells.

An "activated T-cell" or "ATC" is obtained by exposing mononuclear cells in cord blood or another sample containing naïve immune cells to a mitogen, such as phytohemagglutinin (PHA) and/or Interleukin (IL)-2.

An "antigen" includes molecules, such as polypeptides, peptides, or glyco- or lipo-peptides that are recognized by the immune system, such as by the cellular or humoral arms of the immune system. The term "antigen" includes antigenic determinants, such as peptides with lengths of 6, 7, 8, 9, 10, 11, 12, 13, 14, 15, 16, 17, 18, 19, 20, 21, 22 or more amino acid residues that bind to MHC molecules, form parts of MHC Class I or II complexes, or that are recognized when complexed with antigen-presenting molecules.

T Cell Antigen/epitope: An antigen or epitope that is recognized by and triggers an immune response in a T cell (e.g., an antigen that is specifically recognized by a T cell receptor on a T cell via presentation of the antigen or portion thereof bound to a major histocompatibility complex molecule (MHC). T cells antigens generally are proteins or peptides. This term includes peptide antigens recognized by alpha-beta T cells or gamma-delta T cells, as well as lipid, heat-shock proteins, or other stress-induced antigens which may be recognized by gamma-delta T cells. A T cell antigen may be an antigen that stimulates a CD8+ T cell response, a CD4+ T cell response, a gamma delta T-cell response or that stimulates a combination of these.

An "antigen presenting cell (APC)" refers to a class of cells capable of presenting one or more antigens in the form of peptide-MHC complex recognizable by specific effector cells of the immune system, and thereby inducing an effective cellular immune response against the antigen or antigens being presented. Examples of professional APCs are dendritic cells and macrophages, though any cell expressing MHC Class I or II molecules can potentially present a peptide antigen.

A "control" is a reference sample or subject used for purposes of comparison with a test sample or test subject. Positive controls measure an expected response and negative controls provide reference points for samples where no or a background response is expected.

"Cord blood" has its normal meaning in the art and refers to blood that remains in the placenta and umbilical cord after birth and contains hematopoietic stem cells. Cord blood may be fresh, cryopreserved or obtained from a cord blood bank.

The term "cytokine" has its normal meaning in the art. Examples of cytokines used in the invention include IL-2, IL-7 and IL-15.

The term "dendritic cell" or "DC" describes a diverse population of morphologically similar cell types found in a variety of lymphoid and non-lymphoid tissues, see Steinman, Ann. Rev. Immunol. 9:271-296 (1991).[19] Some embodiments of the invention involve dendritic cells and dendritic cell precursors derived from cord blood.

The term "effector cell" describes a cell that can bind to or otherwise recognize an antigen and mediate an immune response. Antigen-specific T cells are effector cells.

"Human papilloma virus" is a DNA virus in the papilloma virus family that infects humans. At least 170 subtypes are known, many of which are transmitted by sexual contact. Types 16, 18, 31, 33, 35, 39, 45, 51, 52, 56, 58, 59, 68, 73, and 82 are carcinogenic "high-risk" sexually transmitted HPVs and may lead to the development of cervical intraepithelial neoplasia (CIN), vulvar intraepithelial neoplasia (VIN), penile intraepithelial neoplasia (PIN), and/or anal intraepithelial neoplasia (AIN).[6, 8, 20-22]

HPV is associated with common warts—HPV types 2 and 4 (most common); also types 1, 3, 26, 29, and 57 and others. Cancers and genital dysplasia—"high-risk" HPV types are associated with cancers, notably cervical cancer, and can also cause some vulvar, vaginal, penile, anal and some oropharyngeal cancers. "Low-risk" types are associated with warts or other conditions. High-risk: 16, 18 (cause the most cervical cancer); also 31, 33, 35, 39, 45, 52, 58, 59, and others. Plantar warts (myrmecia)—HPV type 1 (most common); also types 2, 3, 4, 27, 28, and 58 and others. Anogenital warts (condylomata *acuminata* or venereal warts)—HPV types 6 and 11 (most common); also types 42, 44 and others. Low-risk: 6, 11 (most common); also 13, 44, 40, 43, 42, 54, 61, 72, 81, 89, and others. Flat warts—HPV types 3, 10, and 28. Butcher's warts—HPV type 7. Heck's disease (Focal epithelial hyperplasia)—HPV types 13 and 32.[6, 8, 20-22]

An "infiltrating lymphocyte" is one that has entered a particular biological compartment or tissue, mucosal layer (e.g., epithelium, lamina propia) or skin layer (e.g., stratum corneum, stratum lucidum, stratum *granulosum*, stratum *spinosum*, stratum basate and dermis). These include those infiltrating a neoplasm, tumor or cancer including cervical cancer, anal, penile, oropharyngeal, vulvar, or vaginal cancers. It includes lymphocytes that have infiltrated a papilloma, including squamous cell papilloma, inverted papilloma, urothelial papilloma, intraductal papilloma or the breast, or wart, such as a plantar or genital wart. Antigens recognized by infiltrating lymphocytes may be selected to induce T cells having specificity for HPV related conditions in particular tissues.

The term "isolated" means separated from components in which a material is ordinarily associated with, for example, an isolated cord blood mononuclear cell can be one separated from red blood cells, plasma, and/or other components of cord blood.

"Mucosa" or mucous membranes have their conventional anatomical and physiological meanings. These include ocular mucosal, nasal mucosa, olfactory mucosa, oral mucosa, bronchial mucosa and the lining of vocal folds, esophageal mucosa, gastric mucosa, intestinal mucosa, anal mucosa, penile mucosa, and vaginal mucosa, and endometrium which is the mucosa of the uterus. Mucosa are susceptible to infection by HPV.

A "naive" T-cell or other immune effector cell is one that has not been exposed to an antigen or to an antigen-presenting cell presenting a peptide antigen capable of activating that cell.

A "peptide library" or "overlapping peptide library" within the meaning of the application is a complex mixture of peptides which in the aggregate covers the partial or complete sequence of a protein antigen, especially those of opportunistic viruses. Successive peptides within the mixture overlap each other, for example, a peptide library may be constituted of peptides 15 amino acids in length which overlap adjacent peptides in the library by 11 amino acid residues and which can span the entire length of a protein antigen or select portions of an antigen. Peptide libraries are commercially available and may be custom-made for particular antigens. Methods for contacting, pulsing or loading antigen-presenting cells are well known and incorporated by reference to Ngo, et al. (2014).[23]

The term "precursor cell" refers to a cell which can differentiate, mature, or otherwise be transformed into another kind of cell. For example, a "T-cell precursor cell" can differentiate into a T-cell and a "dendritic precursor cell" can differentiate into a dendritic cell.

A "subject" is a vertebrate, preferably a mammal, more preferably a human. Mammals include, but are not limited to humans, simians, equines, bovines, porcines, canines, felines, murines, other farm animals, sport animals, or pets. Subjects include those in need of antigen-specific T cells, such as those with lymphocytopenia, those who have undergone immune system ablation, those undergoing transplantation and/or immunosuppressive regiments, those having naïve or developing immune systems, such as neonates, or those undergoing cord blood or stem cell transplantation.

Generation of HPV16 E6/E7 Specific T Cells

Overlapping peptide libraries (15-mers overlapping by 11 amino acids) of HPV16-E6 (Protein ID P03126) and HPV16-E7 (P03129) were purchased from JPT Peptide Technologies (Berlin, Germany). Peptides were reconstituted in dimethyl sulfoxide (DMSO) (Sigma-Aldrich, St. Louis, Mo.).

Monocytes were isolated from PBMCs by CD14 selection using MACS Beads (Miltenyi Biotec, San Diego, Calif.) and cultured in 24-well plates ($1 \times 10^6$ cells/well) in DC medium [CellGenix medium (CellGenix GmbH, Freiburg, Germany) and 1% alanyl-glutamine (GlutaMAX; Gibco Life Technologies, Grand Island, N.Y.)], with 800 U/mL granulocyte/macrophage-colony stimulating factor (GM-CSF) (R&D Systems, Minneapolis, Minn.) and 1000 U/mL IL-4 (R&D Systems).

DCs were fed with GM-CSF and IL-4 on day 3. On the morning of day 5, 1 ml of media was removed from the wells and 1 μL peptide mixture (E6 and E7) was added to each of the wells. At least one hour later in the afternoon of day 5, DCs were matured by adding 1 mL of DC media per well with the following cytokines at these final concentrations: 100 ng/mL IL-6 (R&D Systems), 10 ng/mL IL-1β (R&D Systems), 10 ng/mL TNFα (R&D Systems), 1 μg/mL prostaglandin E2 (R&D Systems), 800 U/mL GM-CSF, 1000 U/mL IL-4, and 30 ng/mL LPS.

On day 7, DCs were harvested and re-suspended at $1 \times 10^5$ cells/mL in CTL medium [45% Click's medium (Irvine Scientific, Santa Ana, Calif.), 45% RPMI-1640 (HyClone, Logan, Utah), 10% human AB serum (Gemini BioProducts, West Sacramento, Calif.) and 1% GlutaMAX], CD14 negative PBMCs were thawed and re-suspended at $1 \times 10^6$ cells/mL in CTL medium. Cells were stimulated with peptide-loaded DCs at a 1:10 ratio (DCs:CD14−) in CTL medium with 10 ng/mL IL-6, 10 ng/mL IL-7 (R&D Systems), 10 ng/mL IL-12 (R&D Systems) and 10 ng/mL IL-15 (R&D Systems).

Nine to twelve days after the first stimulation, T cells were harvested, counted and stimulated again at a concentration of $1 \times 10^6$ cells/mL in CTL medium ($1 \times 10^6$ cells/mL per well of 24-well plates) with newly prepared peptide-loaded DCs and IL-7 and IL-15 (or alternatively with IL-7, IL-12, and IL-15, or IL-6, IL-7, IL-12, and IL-15). Cell cultures were supplemented with IL-2 (R&D Systems) if necessary.

Seven days after the second stimulation, T cells were harvested, counted, re-suspended at $2.5 \times 10^5$/mL and stimulated for a third time with newly prepared peptide-loaded DCs and IL-2 and IL-15. Cell cultures were supplemented with alternating IL-2 or IL15 (R&D Systems) if necessary. Alternatively, cells are given other antigen presenting cells mentioned above—also loaded with peptides.

Figure 2:
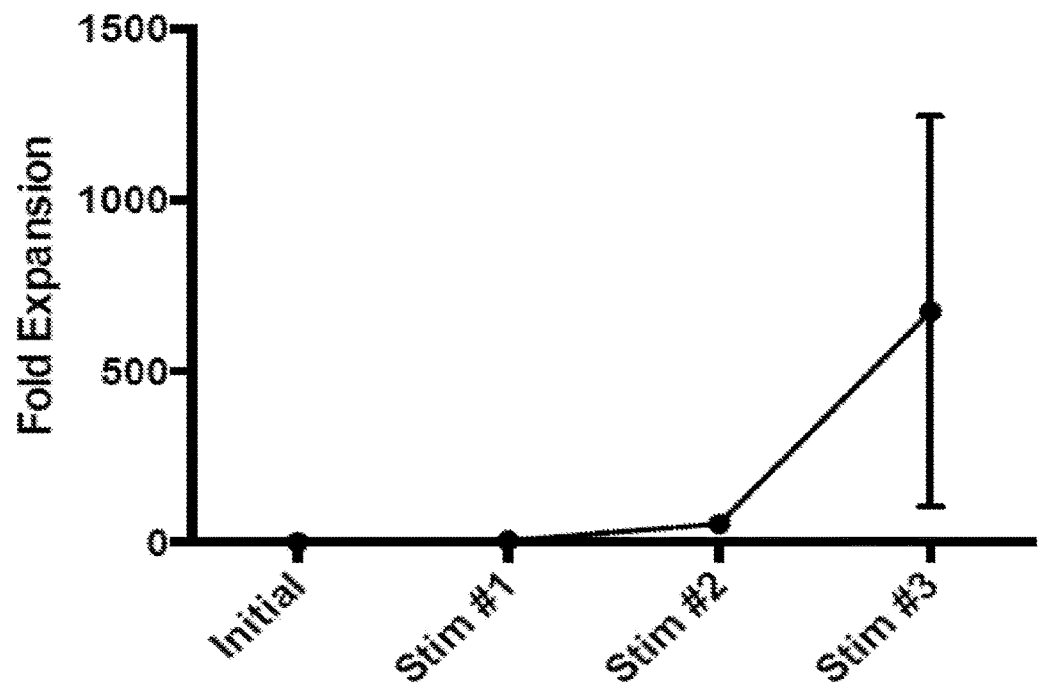
FIG. 2. T cells that recognize HPV (n=5) can be expanded to clinically relevant numbers following three stimulations. This shows that the invention is capable of robustly manufacturing HPV-recognizing or HPV-specific T cells for clinical or other uses.

The HPV-specific T cells produced by this method were evaluated as shown by FIGS. 1-3. These figures show that the method disclosed herein generates T cells from cells obtained from healthy donors not infected by HPV that recognize HPV E6 and E7 antigens. These cells can be expanded as described herein and exhibit cell surface markers that have a mixed phenotype (CD4 and CD8). A mixed phenotype has been shown to promote better responses from T cell infusions. Cells also express the costimulatory receptors CD27 and CD28.

Expression of mixed CD4+CD8+ cell surface markers has been associated with induction of an adaptive immune response against infectious pathogens such as those of multiple past, latent and high-level persistent viral infections. CD4+CD8+ T cells broaden the perception of T cell population involved in antiviral immune responses; Nacimbene, et al., Blood 2004 104:478-486. The methods described herein generate a large numbers of mixed CD4+CD8+ T cells that recognize HPV and may potentially serve as superior effectors of anti-HPV immunity than T cells having other cell surface phenotypes.

Expression of CD4+, CD45RO+ and CD27+ T cell markers is associated with decreased persistence of HPV and with resistance to HPV infection; Rodriguez, et al., Int J Cancer. 2011 Feb. 1; 128(3): 597-607. HPV-specific T cells produced by the method disclosed herein produce may potentially be used to protect subjects having or at risk of acquiring persistent HPV infections. These at risk subjects include smokers, tobacco smokers or users of chewing tobacco, those with poor oral hygiene who are at increased risk of oropharyngeal cancer, those having weakened immune systems, including diseases like HIV, those on immunosuppressive drugs or regimens, such as cancer patients or subjects receiving blood transfusions or tissue transplants, and those at higher risk of cervical cancer including women having multiple children, women using oral contraceptives, especially for a long term. Subjects with diseases, disorders or conditions characterized by chronic inflammation or aged individuals (e.g., at or above 50, 60, 70, or 80 years of age) are also at higher risk of persistent HPV infection than normal subjects.

T cells generated by the methods disclosed herein also contain a high frequency or level of costimulatory receptors CD27 and CD28 as shown in FIG. 3.

T cells expressing CD27 can be costimulated via CD27. Viruses are known to modulate expression of CD27 as a means to evade the host immune system. Generation of T cells expressing CD27 provides a means for these cells to induce virus-specific immunity during acute or persistent viral infection, Welten, et al., J Virol. 2013 June; 87(12): 6851-65. The methods disclosed herein produce large numbers of T cells that recognize HPV antigens that are CD27+ and that would be capable of costimulation via CD27. T-cell persistence is promoted by CD27 costimulation and may improve clinical efficacy of adoptive immunotherapy of subjects (such as those infected with HPV or having persistent HPV infections. Mechanisms accounting for CD27-mediated human T-cell survival in vivo may include upregulation of anti-apoptotic molecules, instructed CD4 help and autocrine IL-2 production by $CD8^+$ T cells in vivo; Song, et al., Oncoimmunology, 2012 Jul. 1; 1(4): 547-549.

T cells expressing CD28 can be costimulated via CD28 during the effector phase of an anti-viral T cell response. T cells that do not express CD28 or in which the CD28 receptor is blocked exhibit decreased responses to virus and result in increased apoptosis and decreased viral clearance; Dolfi, et al., J Immunol. 2011 Apr. 15; 186(8):4599-608. The methods disclosed herein produce large numbers of T cells that recognize HPV antigens that are CD28+ and that would be capable of costimulation via CD28.

The process according to the present invention is broad in scope. For example, it can be used to prevent conditions associated with HPV post allogeneic stem cell transplant, or it can be used to prevent relapse of HPV malignancies like cervical carcinoma. Specific non-limited embodiments of the invention are now further described.

In one embodiment, the invention comprises a process for producing an HPV antigen-specific T cell comprising (a) dividing mononuclear cells from any cell source containing naïve immune cells into several portions; (b) stimulating a portion of said sample with PHA or another mitogen and with IL-2 to produce ATCs activated T cells ("ATCs") that serve antigen presenting functions during subsequent stimulations and optionally treating the ATCs with radiation or another agent to inhibit their outgrowth; (c) separating T cells and T-cell precursor cells (e.g., non-adherent cells, $CD3^+$ cells, $CD14^-$ cells) from dendritic cells and dendritic precursor cells (e.g, adherent cells, $CD11C^+$ or $CD14^+$ cells); (d) cryopreserving or otherwise reserving the T cells and T-cell precursor cells; (e) differentiating the dendritic cells and dendritic precursor cells in the second portion with cytokine(s) or other agent(s) that generate and mature dendritic cells and with at least one HPV peptide antigen or HPV antigen mix to produce antigen-presenting dendritic cells that present at least one HPV peptide antigen, and optionally treating said antigen-presenting dendritic cells with radiation or another agent sufficient to inhibit their outgrowth; (f) stimulating the cryopreserved or otherwise reserved T cells and T-cell precursor cells from (d) with the dendritic antigen-presenting cells produced in (e) in the presence of any combination or all of IL-6, IL-7, IL-12 and IL-15 to produce antigen-specific T cells that recognize the at least one HPV peptide antigen; (g) stimulating antigen-specific T cells produced by (f) with the ATCs of (b) in the presence of the at least one HPV peptide antigen, optionally, in the presence of potentially artificial or alternative antigen presenting cells or other accessory cells in the presence of IL-2 and/or IL-15; optionally, repeating (g) one or more times; and (h) recovering antigen-specific T cells that recognize at least one peptide antigen.

T cells the recognize HPV antigens may be further isolated or purified based on cell surface markers. T cell phenotypes include cells with one or more of the following markers: CD4+, CD8+, CD4+/CD25+, CD45RO+, CD27+, CD28+, and/or PD1. T cell phenotypes include CD4+CD8+; CD27+CD28+ and CD4+, CD45RO+ and CD27+. Cells with undesired phenotypes may be removed or separated from desired HPV recognizing T cells using methods known in the art.

In methods according to the invention it is unnecessary to use viable virus to generate T cells recognizing HPV antigens. In the Examples above no strains of HPV or any live virus were used to produce any of the T cells. The antigens were from JPT: the E6 and E7 antigens were used. Nevertheless, the methods described herein can be practiced with HPV antigens from other sources such as virus infected cell-lysate, whole virus proteins, and plasmids or DNA sequences or viral vectors encoding the HPV antigen.

The process as described in the embodiment above may further comprise separating mononuclear cells containing naïve T cells prior to (a). The mononuclear cells used in this process may be obtained from cord blood, from stem cells, or from other sources of cells naïve to HPV antigens or naïve to particular HPV strains or particular HPV antigens. Thus, the mononuclear cells used in this process may be obtained from hematopoietic stem cells naïve to the at least one HPV peptide antigen; or from a sample containing stem cells, precursor T cells, or T cells from a subject whose immune system is naïve to the at least one HPV peptide antigen.

A process according to the invention may comprise (b) stimulating a first portion of said sample with PHA and with and IL-2 to produce activated T cells ("ATCs"). These ATCs may be cryopreserved or otherwise banked for later use or may be used immediately. Preferably, the ATCs are used fresh and mixed in with antigen-specific T cells produced in (f) without the need to cryopreserve either the ATCs or the antigen-specific T cells. For example, PHA blasts prepared in (b) can be used 14-16 days after initiation of the process to provide a second stimulation to the antigen-specific T cells produced in (f).

While those skilled in the art may select a suitable number of cells for use in a process according to the invention, such a process may comprise stimulating about 1 to 20 million, preferably 5-15 million, most preferably about 8-12 million, mononuclear cord blood cells with PHA and IL-2 in (b). Those of skill in the art may adjust the numbers of cells or other process conditions as necessary to scale up or scale down the process producing T cells recognizing HPV peptide antigens. In a process according to the invention, (b) may comprise producing T-blasts, B-blasts, lymphoblastoid cells, or CD3-CD28 blasts instead of PHA blasts as activated T cells.

Such a process may use T cells and/or T cell precursor cells that are separated from dendritic cells and dendritic precursor cells by culturing the second portion via plastic adherence under conditions sufficient for cells in the second portion to adhere to the cell culture plate or device and then removing T cells and T cell precursor cells from the cell culture plate or device and recovering the dendritic cells and dendritic precursor cells attached to the solid medium. Alternatively, these two populations of cells may be separated magnetically, by the use of antibodies that specifically recognize each population, by CD14-based selection (e.g., using MAC beads) or by other known methods of cell sorting. The separate populations of cells may be cryopreserved or otherwise banked for later use, or may be used immediately to produce T cells or dendritic cells. These populations may also be cryopreserved or otherwise banked after subsequent treatment steps described herein that produce mature dendritic cells loaded with peptide antigens or antigen-specific T cells.

In a process of the invention in (e) the dendritic cells and dendritic precursor cells can be grown in the presence of cytokines necessary for differentiation and maintenance of dendritic cells, including but not limited to IL-4 and GM-CSF; and in (e) the dendritic cells and dendritic precursor cells may be allowed to undergo maturation with a dendritic cell-maturing cytokine or agent selected from the group consisting of, but not limited to, one or more of the following LPS, TNF-alpha, IL-1 beta, IL-6, PGE-1, PGE-2, and other immune adjuvants (e.g. oligonucleotides), along with IL-4 and GM-CSF.

In some embodiments of the invention in or prior to (f) the T cells or T cell precursor cells may be treated to expand CD45RA positive cells; or in or prior to, (f) the T cells and T cell precursors may be treated to deplete CD45RO positive cells. Other T cells with particular markers may be treated to expand or deplete HPV-recognizing T cells having particular cell surface phenotypes, such as any of those phenotypes described herein.

In a process according to the invention, the at least one antigen may comprise a series of overlapping peptides spanning an entire HPV protein or HPV antigen. In some embodiments the antigen-specific T cells may be selected to recognize at least one antigen of an opportunistic HPV that is acquired nosocomially or iatrogenically or that is transmitted to a subject in a hospital (e.g., a hospital acquired infection) or by a particular mode of invention, such as by direct contact with a mucous membrane, skin, or through sexual contact. The at least one peptide antigen may comprise a HPV antigen or peptide library, such as an HPV E1-E5 antigen or peptide library; an HPV E6 or E7 antigen or peptide library; an HPV L1 or L2 antigen or peptide library; or mixtures thereof.

The at least one peptide antigen may be one recognized by a T-cell isolated from a site, tissue or cell infected with HPV.

Another embodiment of the invention is directed to a composition comprising antigen-specific T cells produced by a process according to the invention. Such antigen specific T cells may recognize one, two, three, four, five or more HPV strains, serotypes, antigens or epitopes. Such a composition may comprise mononuclear cells isolated from different cell sources, which preferably mostly comprise but are not limited to samples containing naïve immune cells, antigen presenting cells derived from these same sources, such as dendritic cells, PHA blasts—which contain in them PHA or another mitogen, IL-2, and a medium that maintains the viability of said cells, and, optionally, K562 cells or other non-autologous cells, including artificial or alternative antigen presenting cells, that costimulate T cells, wherein, optionally, said cells have been treated to prevent outgrowth.

In another embodiment the comprising may comprise T cells and T cell precursor cells (e.g., non-adherent cells, $CD3^+$ cells, $CD14^-$ cells) that have been separated from dendritic cells and dendritic precursor cells (e.g, adherent cells, $CD11C^+$ or $CD14^+$ cells) and that are naïve to an HPV peptide antigen; cytokines including but not limited to at least one of IL-2, IL-6, IL-7, IL-12, and IL-15, at various points in the culture period; and a medium that maintains the viability of said T cells and T-cell precursor cells.

Other embodiments of the invention include a bank or cell storage facility which contains one or more samples of T cells that recognize HPV peptide antigens produced by the process of embodiment 1 in combination with a storage or freezing medium; wherein said one or more samples is optionally associated, identified or indexed by information describing its source, including full or partial DNA sequence information, information describing its histocompatibility, including major and/or minor histocompatibility antigens or markers, and/or information about the peptide antigens it contains or recognizes. Such an antigen-specific T cell bank may comprise multiple samples of cryo- or otherwise preserved viable HPV antigen-specific T cells produced by the process of embodiment 1.

Another embodiment of the invention constitutes a kit comprising T cells and T cell precursor cells (e.g., non-adherent cells, $CD3^+$ cells, $CD14^-$ cells) that have been separated from dendritic cells and dendritic precursor cells (e.g, adherent cells, $CD11C^+$ or $CD14^+$ cells) and that are naïve to an HPV peptide antigen; cytokines including but not limited to at least one of IL-2, IL-6, IL-7, IL-12, and IL-15; a medium that maintains the viability of said T cells and T-cell precursor cells; dendritic or dendritric precursor cells that have been separated from said T cells and T cell precursor cells; a medium that maintains the viability of said dendritic or dendritic precursor cells; K562 cells, artificial or alternative antigen presenting cells, other non-autologous cells that costimulate T cells, optionally treated to prevent outgrowth, and at least one HPV peptide antigen or mixture of HPV peptides.

The foregoing description discloses particular embodiments. As will be understood by those skilled in the art, the approaches, methods, techniques, materials, devices, and so forth disclosed herein may be embodied in additional embodiments as understood by those of skill in the art, it is the intention of this application to encompass and include such variation. Accordingly, this description is illustrative and should not be taken as limiting the scope of the following claims. Citations herein are incorporated by reference especially for the purposes of specifically describing the referenced subject matter or the subject matter in the same or adjoining paragraphs or sections.

REFERENCES

1. Leen A M, Bollard C M, Mendizabal A M, et al. Multicenter study of banked third-party virus-specific T cells to treat severe viral infections after hematopoietic stem cell transplantation. *Blood.* 2013; 121:5113-5123.
2. Foster A E, Dotti G, Lu A, et al. Antitumor activity of EBV-specific T lymphocytes transduced with a dominant negative TGF-beta receptor. *Journal of Immunotherapy.* 2008; 31:500-505.
3. Heslop H E, Slobod K S, Pule M A, et al. Long-term outcome of EBV-specific T-cell infusions to prevent or treat EBV-related lymphoproliferative disease in transplant recipients. *Blood.* 2010; 115:925-935.
4. Melenhorst J J, Castillo P, Hanley P J, et al. Graft versus leukemia response without graft-versus-host disease elicited by adoptively transferred multivirus-specific T-cells. *Molecular therapy: the journal of the American Society of Gene Therapy.* 2015; 23:179-183.
5. Rooney C M, Leen A M, Vera J F, Heslop H E. T lymphocytes targeting native receptors. *Immunological reviews.* 2014; 257:39-55.
6. Stanley M A, Pett M R, Coleman N. HPV: from infection to cancer. *Biochemical Society Transactions.* 2007; 35:1456-1460.
7. Stanley M A, Sterling J C. Host responses to infection with human papillomavirus. *Current problems in dermatology.* 2014; 45:58-74.
8. Stanley M. Immunobiology of HPV and HPV vaccines. *Gynecologic oncology.* 2008; 109:S15-21.
9. Furniss C S, McClean M D, Smith J F, et al. Human papillomavirus 16 and head and neck squamous cell carcinoma. *International Journal of Cancer.* 2007; 120: 2386-2392.
10. Psyrri A, DiMaio D. Human papillomavirus in cervical and head-and-neck cancer. *Nature Clinical Practice Oncology.* 2008; 5:24-31.
11. Miralles-Guri C, Bruni L, Cubilla A L, Castellsague X, Bosch F X, de Sanjose S. Human papillomavirus prevalence and type distribution in penile carcinoma. *Journal of Clinical Pathology.* 2009; 62:870-878.
12. Ramos C A, NaralaN, Vyas G M, et al. Human papillomavirus type 16 E6/E7-specific cytotoxic T lymphocytes for adoptive immunotherapy of HPV-associated malignancies. *J Immunother.* 2013; 36:66-76.
13. de Jong A, van Poelgeest M I, van der Hulst J M, et al. Human papillomavirus type 16-positive cervical cancer is associated with impaired CD4+ T-cell immunity against early antigens E2 and E6. *Cancer research.* 2004; 64:5449-5455.
14. Hoots B E, Palefsky J M, Pimenta J M, Smith J S. Human papillomavirus type distribution in anal cancer and anal intraepithelial lesions. *International Journal of Cancer.* 2009; 124:2375-2383.
15. Liu G, Markowitz L E, Hariri S, Panicker G, Unger E R. Seroprevalence of 9 Human Papillomavirus Types in the United States, 2005-2006. *The Journal of infectious diseases.* 2015.
16. Hanley P J, Melenhorst J J, Nikiforow S, et al. CMV-specific T cells generated from naive T cells recognize atypical epitopes and may be protective in vivo. *Science translational medicine.* 2015; 7:285ra263.
17. Hanley P J, Lam S, Shpall E J, Bollard C M. Expanding cytotoxic T lymphocytes from umbilical cord blood that target cytomegalovirus, Epstein-Barr virus, and adenovirus. *Journal of visualized experiments: JoVE.* 2012: e3627.
18. Papadopoulou A, Gerdemann U, Katari U L, et al. Activity of broad-spectrum T cells as treatment for AdV, EBV, CMV, BKV, and HHV6 infections after HSCT. *Science translational medicine.* 2014; 6:242ra283.
19. Steinman R M. The dendritic cell system and its role in immunogenicity. *Annual review of immunology.* 1991; 9:271-296.
20. Moodley M. Update on pathophysiologic mechanisms of human papillomavirus. *Current opinion in obstetrics & gynecology.* 2005; 17:61-64.
21. Cooper K, McGee J O. Human papillomavirus, integration and cervical carcinogenesis: a clinicopathological perspective. *Molecular pathology: MP.* 1997; 50:1-3.
22. Lowy D R, Schiller J T. Human papillomavirus biology. *Journal of the National Cancer Institute. Monographs.* 1996:141-143.
23. Ngo M C, Ando J, Leen A M, et al. Complementation of antigen-presenting cells to generate T lymphocytes with broad target specificity. *J Immunother.* 2014; 37:193-203.

We claim:
1. A method for treating or preventing an infection by human papillomavirus (HPV) in a subject, comprising:
administering to the subject an HPV antigen-specific T cell population, wherein the HPV antigen-specific T cell population is prepared by a method comprising:
(a) dividing mononuclear cells from a donor source containing immune cells naïve to an HPV antigen into a CD14-positive cell population and a CD14-negative cell population;
(b) culturing a first portion of the CD14-positive cell population in a medium comprising granulocyte/macrophage-colony stimulating factor (GM-CSF) and IL-4 to produce a first population of dendritic cells;
(c) culturing the first population of dendritic cells produced in step (b) in a medium comprising peptides derived from two or more HPV antigens;
(d) culturing the first population of dendritic cells from step (c) in a medium comprising IL-6, IL-1β, TNFα, prostaglandin E2, GM-CSF, IL-4, and LPS;
(e) culturing the CD14-negative cell population with the first population of dendritic cells from step (d) in a medium comprising IL-6, IL-7, IL-12, and IL-15 to produce an HPV-antigen specific T-cell population;

(f) culturing the HPV-antigen specific T-cell population from step (e) with a second population of dendritic cells in a medium comprising IL-7 and IL-15, wherein the second population of dendritic cells are generated from a second portion of the CD-14 positive cell population as provided in steps (b)-(d);

(g) culturing the HPV-antigen specific T-cell population from step (f) with a third population of dendritic cells in a medium comprising IL-2 and IL-15, wherein the third population of dendritic cells are generated from a third portion of the CD-14 positive cell population as provided in steps (b)-(d); and, (h) recovering the HPV-antigen specific T cell population from step (g);

wherein the recovered HPV-antigen specific T-cell population comprises a mixed phenotype of CD4+ and CD8+ T-cells, and, wherein the recovered HPV-antigen specific T-cell population comprises CD27+ and CD28+ T-cells.

2. The method of claim 1, wherein the two or more HPV antigens are selected from the group consisting of E1, E2, E3, E4, E5, E6, E7, L1, and L2.

3. The method of claim 2, wherein the two or more HPV antigens comprise E6 and E7.

4. The method of claim 1, wherein the peptides derived from the two or more HPV antigens are from overlapping peptide libraries.

5. The method of claim 1, wherein the medium of step (f) further comprises IL-6 or IL-12.

6. The method of claim 1, wherein the medium of step (f) further comprises IL-6 and IL-12.

7. The method of claim 1, wherein the medium of step (f) further comprises IL-2.

8. The method of claim 5, wherein the medium of step (f) further comprises IL-2.

9. The method of claim 6, wherein the medium of step (f) further comprises IL-2.

10. The method of claim 1, wherein the medium of step (g) further comprises IL-2 or IL-15.

11. The method of claim 1, wherein the medium of step (g) is supplemented with IL-2 and IL-15, wherein the IL-2 and IL-15 are added to the medium in an alternating schedule.

12. A composition comprising an HPV antigen-specific T cell population and a medium that maintains the viability of the T cell population, wherein the HPV antigen-specific T cell population is prepared by a method comprising:

(a) dividing mononuclear cells from a donor source containing immune cells naïve to an HPV antigen into a CD14-positive cell population and a CD14-negative cell population;

(b) culturing a first portion of the CD14-positive cell population in a medium comprising granulocyte/macrophage-colony stimulating factor (GM-CSF) and IL-4 to produce a first population of dendritic cells;

(c) culturing the first population of dendritic cells produced in step (b) in a medium comprising peptides derived from two or more HPV antigens;

(d) culturing the first population of dendritic cells from step (c) in a medium comprising IL-6, IL-1β, TNFα, prostaglandin E2, GM-CSF, IL-4, and LPS;

(e) culturing the CD14-negative cell population with the first population of dendritic cells from step (d) in a medium comprising IL-6, IL-7, IL-12, and IL-15 to produce an HPV-antigen specific T-cell population;

(f) culturing the HPV-antigen specific T-cell population from step (e) with a second population of dendritic cells in a medium comprising IL-7 and IL-15, wherein the second population of dendritic cells are generated from a second portion of the CD-14 positive cell population as provided in steps (b)-(d);

(g) culturing the HPV-antigen specific T-cell population from step (f) with a third population of dendritic cells in a medium comprising IL-2 and IL-15, wherein the third population of dendritic cells are generated from a third portion of the CD-14 positive cell population as provided in steps (b)-(d); and, (h) recovering the HPV-antigen specific T cell population from step (g);

wherein the recovered HPV-antigen specific T-cell population comprises a mixed phenotype of CD4+ and CD8+ T-cells, and, wherein the recovered HPV-antigen specific T-cell population comprises CD27+ and CD28+ T-cells.

13. A method for treating or preventing an infection by human papillomavirus (HPV) in a subject, comprising:

administering to the subject an HPV antigen-specific T cell population, wherein the HPV antigen-specific T cell population is prepared by a method comprising:

(a) dividing mononuclear cells from a donor source containing immune cells naïve to an HPV antigen into a CD14-positive cell population and a CD14-negative cell population;

(b) culturing a first portion of the CD14-positive cell population in a medium comprising granulocyte/macrophage-colony stimulating factor (GM-CSF) and IL-4 to produce a first population of dendritic cells;

(c) culturing the first population of dendritic cells produced in step (b) in a medium comprising the peptides derived from two or more HPV antigens;

(d) culturing the first population of dendritic cells from step (c) in a medium comprising IL-6, IL-1β, TNFα, prostaglandin E2, GM-CSF, IL-4, and LPS;

(e) culturing a first portion of the CD14-negative cell population with the first population of dendritic cells from step (d) in a medium comprising IL-6, IL-7, IL-12, and IL-15 to produce an HPV-antigen specific T-cell population;

(f) culturing a second portion of the CD14-negative cell population in a medium with phytohemagglutinin and IL-2 to produce a first population of activated T-cells (ATCs);

(g) culturing the HPV-antigen specific T-cell population from step (e) with the first population of ATCs from step (f) in a medium comprising the two or more HPV antigens, IL-2 or IL-15, or IL-2 and IL-15;

(h) culturing the HPV-antigen specific T-cell population from step (g) with a second population of ATCs in a medium comprising the two or more HPV antigens, IL-2 or IL-15, or IL-2 and IL-15; wherein the second population of ATCs is generated from a third portion of the CD-14 negative cell population as provided in step (f); and, (i) recovering the HPV-antigen specific T cell population from step (h);

wherein the recovered HPV-antigen specific T-cell population comprises a mixed phenotype of CD4+ and CD8+ T-cells, and, wherein the recovered HPV-antigen specific T-cell population comprises CD27+ and CD28+ T-cells.

14. The method of claim 13, wherein the two or more HPV antigens are selected from the group consisting of E1, E2, E3, E4, E5, E6, E7, L1, and L2.

15. The method of claim 13, wherein the two or more HPV antigens comprise E6 and E7.

16. The method of claim 13, wherein the peptides derived from the two or more HPV antigens are from overlapping peptide libraries.

17. The method of claim 13, wherein the medium of step (g) is supplemented with IL-2.

18. The method of claim 13, wherein the medium of step (g) is supplemented with IL-15.

19. The method of claim 13, wherein the medium of step (g) is supplemented with IL-2 and IL-15.

20. The method of claim 13, wherein the culture of step (g) further comprises K562 cells.

21. The method of claim 13, wherein the culture of step (h) further comprises K562 cells.

22. A composition comprising an HPV antigen-specific T cell population and a medium that maintains the viability of the T cell population, wherein the HPV antigen-specific T cell population is prepared by a method comprising:
 (a) dividing mononuclear cells from a donor source containing immune cells naïve to an HPV antigen into a CD14-positive cell population and a CD14-negative cell population;
 (b) culturing a first portion of the CD14-positive cell population in a medium comprising granulocyte/macrophage-colony stimulating factor (GM-CSF) and IL-4 to produce a first population of dendritic cells;
 (c) culturing the first population of dendritic cells produced in step (b) in a medium comprising the peptides derived from two or more HPV antigens;
 (d) culturing the first population of dendritic cells from step (c) in a medium comprising IL-6, IL-1β, TNFα, prostaglandin E2, GM-CSF, IL-4, and LPS;
 (e) culturing a first portion of the CD14-negative cell population with the first population of dendritic cells from step (d) in a medium comprising IL-6, IL-7, IL-12, and IL-15 to produce an HPV-antigen specific T-cell population;
 (f) culturing a second portion of the CD14-negative cell population in a medium with phytohemagglutinin and IL-2 to produce a first population of activated T-cells (ATCs);
 (g) culturing the HPV-antigen specific T-cell population from step (e) with the first population of ATCs from step (f) in a medium comprising the two or more HPV antigens, IL-2 or IL-15, or IL-2 and IL-15;
 (h) culturing the HPV-antigen specific T-cell population from step (g) with a second population of ATCs in a medium comprising the two or more HPV antigens, IL-2 or IL-15, or IL-2 and IL-15; wherein the second population of ATCs is generated from a third portion of the CD-14 negative cell population as provided in step (f); and,
 (i) recovering the HPV-antigen specific T cell population from step (h);
 wherein the recovered HPV-antigen specific T-cell population comprises a mixed phenotype of CD4+ and CD8+ T-cells, and, wherein the recovered HPV-antigen specific T-cell population comprises CD27+ and CD28+ T-cells.

23. A method for treating or preventing an infection by human papillomavirus (HPV) in a subject, comprising:
 administering to the subject an HPV antigen-specific T cell population, wherein the HPV antigen-specific T cell population is prepared by a method comprising:
 (a) dividing mononuclear cells from a naïve donor source containing immune cells naïve to an HPV antigen into a CD14-positive cell population and a CD14-negative cell population;
 (b) culturing a first portion of the CD14-positive cell population in a medium comprising granulocyte/macrophage-colony stimulating factor (GM-CSF) and IL-4 to produce a first population of dendritic cells;
 (c) culturing the first population of dendritic cells produced in step (b) in a medium comprising peptides derived from two or more HPV antigens;
 (d) culturing the first population of dendritic cells from step (c) in a medium comprising IL-6, IL-1β, TNFα, prostaglandin E2, GM-CSF, IL-4, and LPS;
 (e) culturing the CD14-negative cell population with the first population of dendritic cells from step (d) in a medium comprising IL-6, IL-7, IL-12, and IL-15 to produce an HPV-antigen specific T-cell population;
 (f) culturing the HPV-antigen specific T-cell population from step (e) with a second population of dendritic cells in a medium comprising IL-7 and IL-15, wherein the second population of dendritic cells are generated from a second portion of the CD-14 positive cell population as provided in steps (b)-(d);
 (g) culturing the HPV-antigen specific T-cell population from step (I) with a third population of dendritic cells in a medium comprising IL-2 and IL-15, wherein the third population of dendritic cells are generated from a third portion of the CD-14 positive cell population as provided in steps (b)-(d); and,
 (h) recovering the HPV-antigen specific T cell population from step (g);
 wherein the recovered HPV-antigen specific T-cell population comprises a mixed phenotype of CD4+ and CD8+ T-cells, and,
 wherein the recovered HPV-antigen specific T-cell population comprises CD27+ and CD28+ T-cells.

24. The method of claim 23, wherein in (e) cytokines in the medium consist of IL-6, IL-7, IL-12, and IL-15.

25. The method of claim 23, wherein in (f) cytokines in the medium consist of IL-7 and IL-15.

26. A composition comprising an HPV antigen-specific T cell population, wherein the HPV antigen-specific T cell population is prepared by a method comprising:
 (a) dividing mononuclear cells from a naïve donor source containing immune cells naïve to an HPV antigen into a CD14-positive cell population and a CD14-negative cell population;
 (b) culturing a first portion of the CD14-positive cell population in a medium comprising granulocyte/macrophage-colony stimulating factor (GM-CSF) and IL-4 to produce a first population of dendritic cells;
 (c) culturing the first population of dendritic cells produced in step (b) in a medium comprising peptides derived from two or more HPV antigens;
 (d) culturing the first population of dendritic cells from step (c) in a medium comprising IL-6, IL-1β, TNFα, prostaglandin E2, GM-CSF, IL-4, and LPS;
 (e) culturing the CD14-negative cell population with the first population of dendritic cells from step (d) in a medium comprising IL-6, IL-7, IL-12, and IL-15 to produce an HPV-antigen specific T-cell population;
 (f) culturing the HPV-antigen specific T-cell population from step (e) with a second population of dendritic cells in a medium comprising IL-7 and IL-15, wherein the second population of dendritic cells are generated from a second portion of the CD-14 positive cell population as provided in steps (b)-(d);

(g) culturing the HPV-antigen specific T-cell population from step (f) with a third population of dendritic cells in a medium comprising IL-2 and IL-15, wherein the third population of dendritic cells are generated from a third portion of the CD-14 positive cell population as provided in steps (b)-(d); and, (h) recovering the HPV-antigen specific T cell population from step (g);

wherein the recovered HPV-antigen specific T-cell population comprises a mixed phenotype of CD4+ and CD8+ T-cells, and, wherein the recovered HPV-antigen specific T-cell population comprises CD27+ and CD28+ T-cells.

* * * * *